(12) United States Patent
Stark et al.

(10) Patent No.: US 10,549,021 B2
(45) Date of Patent: Feb. 4, 2020

(54) PERISTALTIC PUMP AND PUMPING METHOD, IN PARTICULAR FOR USE AS IMPLANT

(71) Applicant: ETH Zurich, Zurich (CH)

(72) Inventors: Wendelin Jan Stark, Langenthal (CH); Christoph Schumacher, Zurich (CH); Roland Fuhrer, Zurich (CH); Michael Loepfe, Zurich (CH)

(73) Assignee: ETH Zurich, Zurich (CH)

( * ) Notice: Subject to any disclaimer, the term of this patent is extended or adjusted under 35 U.S.C. 154(b) by 22 days.

(21) Appl. No.: 15/033,377

(22) PCT Filed: Oct. 1, 2014

(86) PCT No.: PCT/CH2014/000141
§ 371 (c)(1),
(2) Date: Apr. 29, 2016

(87) PCT Pub. No.: WO2015/066824
PCT Pub. Date: May 14, 2015

(65) Prior Publication Data
US 2016/0250401 A1    Sep. 1, 2016

(30) Foreign Application Priority Data
Nov. 7, 2013    (EP) .................................... 13005256

(51) Int. Cl.
*A61M 1/10*    (2006.01)
*A61M 1/12*    (2006.01)
*F04B 43/12*    (2006.01)
*F04B 15/00*    (2006.01)
*F04B 9/109*    (2006.01)
*F04B 9/129*    (2006.01)
*F04B 43/02*    (2006.01)
*F04B 43/14*    (2006.01)
(Continued)

(52) U.S. Cl.
CPC .............. *A61M 1/12* (2013.01); *A61M 1/106* (2013.01); *A61M 1/1039* (2014.02);
(Continued)

(58) Field of Classification Search
CPC ....................................................... A61M 1/10
See application file for complete search history.

(56) References Cited

U.S. PATENT DOCUMENTS 4,886,514 A * 12/1989 Maget ............... A61M 5/14276
604/20
5,571,261 A    11/1996 Sancoff et al.

FOREIGN PATENT DOCUMENTS

| EP | 0209644 | 1/1987 |
| GB | 2010385 | 6/1979 |
| WO | 02093665 | 11/2002 |

OTHER PUBLICATIONS

PCT International Search Report No. PCT/CH2014/000141, dated Jan. 8, 2015 completed on Dec. 12, 2014.
(Continued)

*Primary Examiner* — Matthew W Schall
(74) *Attorney, Agent, or Firm* — Cooper & Dunham LLP

(57) ABSTRACT

A pump having at least a fluid pump chamber (11) and a first driver chamber (12) separated from the fluid pump chamber (11) by an elastic wall (13, 13-1, 13-2) is described with the first driver chamber (12) expanding after a chemical reaction between fuel and oxidant and driving through deformation of the elastic wall fluid out of the fluid pump chamber (11), with the main parts of the pump being made of an elastic material to be used for example as a body implant.

16 Claims, 4 Drawing Sheets

(52) U.S. Cl.
CPC ........... *A61M 1/1046* (2013.01); *F04B 9/109* (2013.01); *F04B 9/129* (2013.01); *F04B 15/00* (2013.01); *F04B 43/026* (2013.01); *F04B 43/12* (2013.01); *F04B 43/14* (2013.01); *A61M 1/1037* (2013.01); *A61M 1/1098* (2014.02); *A61M 1/122* (2014.02); *A61M 2205/04* (2013.01); *A61M 2210/125* (2013.01)

(56) References Cited

OTHER PUBLICATIONS

Mark S. Slaughter, MD, et al., "Advanced Heart Failure Treated with Continuous-Flow Left Ventricular Assist Device", The New England Journal of Medicine, Published Nov. 17, 2009, pp. 2241-2251.

William L. Holman, MD, et al., Durability of Left Ventricular Assist Devices: Interagency Registry for Mechnically Assisted Circulatory Support (INTERMACS) 2006 to 2011, The Journal of Thoracic and Cardiovascular Surgery, vol. 146, No. 2, pp. 437-441.

Ares Krishna Menon et al., "Circulatory Assist Device", Encyclopedia of Intensive Care Medicine, DOI 10.1007/978-3-642-00418-6, © Springer-Verlag Berlin Heidelberg 2012, pp. 559-566.

C. Stamm et al., "Chapter 17 Total Artificial Heart", Translational Approach to Heart Failure, DOI 10.1007/978-1-4614-7345-9_17, © Springer Science+Business Media New York 2013, 437-447.

International Preliminary Report on Patentability for PCT/CH2014/000141 dated May 19, 2016.

* cited by examiner

PERISTALTIC PUMP AND PUMPING METHOD, IN PARTICULAR FOR USE AS IMPLANT

CROSS REFERENCE TO RELATED APPLICATIONS

This application is a § 371 national stage of PCT International Application No. PCT/CH2014/000141, filed Oct. 1, 2014, claiming priority of European Patent Application 13005256.6, filed Nov. 7, 2013, the contents of each of which are incorporated herein by reference in their entireties.

FIELD OF THE INVENTION

The present invention relates to a pump and a method of operating a pump, particularly as an implant into the human body or as a system to pump shear-sensitive fluids.

BACKGROUND OF THE INVENTION

Movement of liquids is a key function of most technical systems, many medical devices and numerous consumer goods. Traditionally, liquids can be moved either continuously, or in a pulsating flow. Most technical liquids (e.g. water, gasoline) are very tolerant to the resulting mechanical stress when accelerating the liquid and transporting it, usually through a tubular system and/or valves.

Some liquids, however, are sensitive to shear stress, i.e. the fact that parts of the liquid move faster than other, adjacent parts of the liquid, or an adjacent mechanically rigid wall. The liquids or liquid systems of this class, therefore, are difficult to pump and special care is needed to avoid damage to the liquid. Important examples of such sensitive liquids are, ordered according to fields:

- Culture liquids in biotechnological reactors for cultivation of microorganism or cells. Such dispersions need movement to facilitate transport of metabolites, injection of oxygen and removal of carbon dioxide.
- Liquid systems containing fillers, e.g. as found in lacquers or coatings, where particulate material offer part of a design benefit. Typical examples are metal-microplatelet containing surface coating for car bodies, or dispersions containing a drug of low solubility.
- Food, particularly milk and other diary products.
- Blood.

In addition to applying some amount of shear stress, any pump requires an energy supply that provides the necessary energy to apply a force onto the liquid. Hence, in order to move a liquid, a pump needs to convert a source of primary energy input into mechanical movement. During pumping, the pump must in one way or the other apply a force onto the liquid. This transfer induces shear stress, thus making the design of a pump for shear-sensitive liquids challenging.

There are a broad number of technically realized designs for pumps. The large majority of currently used pumps are based on solid components, such as cylinders, pistons, blades and other rotary parts such as propellers or impellers. The use of hard materials, however, inherently creates higher shear gradients as shear is the ratio of change in velocity gradient over distance, since a hard material does not yield (deform). In contrast to this, a soft material mechanically adapts to mechanical stress This can best intuitively be understood when comparing two examples: An iron nail is applied against the palm of a human hand. The nail does not deform, and the pressure applied results in a deformation of the soft biological tissue. In contrast, if a soft rubber stick is pressed against the palm of a human hand, both the soft rubber stick and the human hand are adapting to the force, and both deform. The same happens when a liquid is moved: A ship with a brass propeller and a diesel engine conveys force on the water of a lake by successively displacing water through pushing the hard blades of the propeller through the water. The water, in return, undergoes heavy sheer, often undergoes cavitation (formation of bubbles), and the water stream going off the propeller area is usually highly turbulent, and contains a lot of air bubbles. In contrast, a seal swimming through water has soft paws that deform during swimming, i.e. when the seal applies a force onto the water and moves its body forward. The water behind a swimming seal undergoes no cavitation, and is characterized by well structured vortices, that contain little or no air bubbles.

A specific type of pumps is known as peristaltic pump. In a peristaltic pump the fluid is contained within a flexible tube fitted inside a circular pump casing (though linear peristaltic pumps have been made). A rotor with a number of "rollers", "shoes", "wipers", or "lobes" attached to the external circumference of the rotor compresses the flexible tube. As the rotor turns, the part of the tube under compression is pinched closed (or "occludes") thus forcing the fluid to be pumped to move through the tube. Additionally, as the tube opens to its natural state after the passing of the cam ("restitution" or "resilience") fluid flow is induced to the pump. This process is called peristalsis and is used in many biological systems such as the gastrointestinal tract.

The second key issue when designing efficient pumps is how to convert primary energy into movement. This issue is particularly pressing when pump and primary energy for driving the pump must be transported (i.e. in portable systems, or on-board systems). A particularly challenging pumping application are human heart assist devices (technical devices that help the heart of patients to move the blood through the body) or artificial heart implants such as total implants or artificial hearts, which are herein understood as a technical device pumping a patient's blood through the body, whether placed inside the body as implant or as part of life support system attached via fluid transporting tubes to a patient's circulation system. In many of these challenging applications, the available space in the thorax of a patient, or (less preferred) in the lower intestinal space, is extremely limited and a pump has to be of small volume and simultaneously very efficient to be considered as suitable.

The first generation of pumps used to replace human hearts (e.g. HeartMate I) were pulsatile devices based on a two-chamber design, where the chambers were separated by a membrane. One chamber is used for pumping the blood, while the other is filled with a gas. The gas was used to deform the membrane by changing its pressure, and thus change the volume in the blood chamber, which results in movement of the blood. This approach is similar to the biological design of the human heart since later also contains two chambers, but clinical studies showed that the design was insufficient, as patients suffered from infection (28%) and 35% of all cases underwent a failure of the device. Anticoagulants had to be applied at all times, and result in a significant number of strokes as a side-effect of the blood thinner. This design was so big, that most of it was used extracorporeal (i.e. the patient had the pump above the chest, and needed to carry a larger pump and battery pack.

A second and third generation of heart assist and replacement devices (so called mechanical circulatory support (MCS) devices) is based on the use of continuous flow, (cf)

pumps, e.g. as described in N Engl J Med 2009 361 2241-51 and had a much better clinical outcome. The performance of a technical device is usually compared to the outcome of a heart transplantation which results in a survival of 84, or 80% of the patients after 1 or 2 years, respectively. The current miniaturization of the cf pumps results in higher and higher blade speed, and associated high shear stress. This is clinically evident through the appearance of pump thrombosis that is responsible for 54% of all cases where patients died as described in J Thorac Cardiovasc Surg, 2013, Volume 146, pages 437-441. This study gives recommendations, e.g. to reduce shear force, and if somehow possible, to avoid the use of a so called drive line. Later is an energy feed line (usually an electrical cable) that must go through the patients skin. Particularly this area is often responsible for infections, often with lethal outcome for the patient. Examples of such cf pumps are available from the company heartware. Arrow International (LionHeart) and Abiomed (Abiocor) circumvent this problem by using transcutaneous induction-based energy transfer, but suffered from low patient survival rate, and devices are very large.

WO 02/093665 describes a fuel cell where carbon dioxide is produced as a waste product and used for operating a pump. The carbon dioxide is used to cyclically move an actuator, which in turn cyclically increases and decreases the volume of a pumping chamber.

GB 2010385 relates to a pump where pulsating exhaust gases from a combustion engine are fed to an actuation chamber, where the cyclically move a membrane separating the actuation chamber from a pump chamber.

In the view of the above problems it is seen as an object of the invention to provide a simple pump and pumping methods, particularly for shear-sensitive liquids. In particular it is desirable to provide a pump with fully biocompatible surface, capable of avoiding thrombosis, and to pump blood in a physiologically acceptable shear-rate, so that no anti-coagulant needed, hence reducing the changes for stroke, and avoid bleeding.

SUMMARY OF THE INVENTION

At least some of the above objects are addressed according to a first aspect of the invention by providing a peristaltic pump driven be a volume expansion following a chemical reaction between fuel and oxidant. The term "peristaltic" is chosen to indicate that the pump chamber through which the fluid is pumped has at least partly flexible exterior walls.

The reaction takes place directly in a driver chamber. It comprises one or more ports for fuel or oxidant containing fluids to enter and for exhaust fluids to leave the chamber.

The driver chamber preferably shares an inter-chamber wall with a fluid pump chamber such that deformation of the inter-chamber wall decreases or increases the volume of the pump chamber. In such embodiments, the inter-chamber wall is best less stiff than other, exterior walls of the chambers.

Driver chambers and pump chambers can be arranged as pairs, for example such that a driver chamber acts predominantly or even exclusively onto the pump chamber with which it is paired. In a variant of this embodiment, a pump can have two pump and two driver chambers, preferably with the two driver chamber having different inner volume. A further variant of this embodiment the driver chambers are located around a core volume of the pump occupied by the pump chambers. This variant can be regarded as a concentric pump design with central pump chambers.

In another preferred embodiment one pump chamber is associated (and hence co-located) with two driver chambers.

The pump includes best an ignition controller which controls the timing of reactions associated with different driver chambers to control the pumping operation of the pump. The ignition controller can be adapted to provide the initial energy to initiate a chemical reaction, for example in form of a spark, or control the supply and/or exhaust of fuel and/or oxidant. The latter is particularly preferred in variants of the pump for which the reaction is self-igniting.

Catalytic material can be placed at the desired location of the chemical reaction, particularly within a driver chamber, to promote the reaction or self-ignition.

For pumping shear-sensitive liquids and particularly for applications as implant, it is preferred that the material of the pump components, i.e. of the fluid pump chamber, driver chambers and their permanent content, consists of at least 80%, preferably above 90%, of a soft material such as the elastomeric materials referred to above. The material can further include base material with embedded fibers, for example in locations which are designed to have a higher stiffness than other locations made of the same base materials.

Preferably the above components, at least however the fluid pump chamber, driver chambers and ports connecting these chambers to the exterior are made of a single material, more preferably of a soft material such as the elastomeric materials referred to above. When made of the same material, the walls between chambers are designed to be easier deformable than the walls between the chambers and the exterior, i.e. the same tensile force or pressure applied lead to a greater deformation of an inter-chamber wall than an exterior wall.

In another embodiment, the pumps described herein are useful for the transport of water, waste water, sludge, or other fluids, e.g. in agricultural settings. Here, the pump is usually connected at its exit with a tube that guides the liquid to a final site of use, e.g. a truck, an irrigation channel, a biotechnological reactor, or a feed line in an animal facility. In such application, a soft, combustion driven pump can in principle replace many classical rotary or piston driven pumps. A key advantage of this alternative is its simple design, particularly if made from few elastomers or even a single elastomer. Such simple design is advantageous over classical (hard, metal and hard plastic component based) pumps, as it avoids sealing problems (e.g. in a piston pump, between the moving cylinder head and the wall; in classical rotary pumps, the driver shaft must be sealed against liquid leakage). It is well understood, that magnetic couplings, for example as used in Tapflo® CTM pumps (Steinle-Pumpen, Düsseldorf, Germany), can solve such shaft sealing problems, but they are more complex and have high production costs. In rough environments (e.g. agriculture), pumps can be manufactured out of suitable elastomers or rubbers as known from the manufacturing of tires (automotive tires). Here, potential reinforcement of the pump can be done with brass-coated steel wires, similar to rubber tires manufactured by the company Michelin®.

In yet another embodiment, the described pumps are advantageous used in applications where chemically very reactive liquids must be pumped, or if very dangerous liquids must be transported, particularly if containment of the liquid is an health or safety issue, and current sealing methods are insufficient, or very costly (e.g. through the use of crosslinked fluoropolymers, which provide a very good sealing, but are very expensive to manufacture.) For example, silicon rubber based pumps in accordance with this embodiment can be very corrosion resistant.

In yet another embodiment, the pumps are advantageous applied in conveying suspensions, as they combine independence from sealing (particulate matter usually creates problems in and at seals), and avoid wear, a typical problem in classical, hard wheel-driven peristaltic pumps such as P_classicplus-twin of Ponndorf Geräte-technik GmbH, Kassel Germany, or ALH 10 (Steinle-Pumpen). In the known designs, wear is often a result of the severe deformation of the polymer tube by the external driver wheels and can be avoided using an embodiment of the present invention.

The above and other aspects of the present invention together with further advantageous embodiments and applications of the invention are described in further details in the following description and figures.

DETAILED DESCRIPTION

Figure 1:
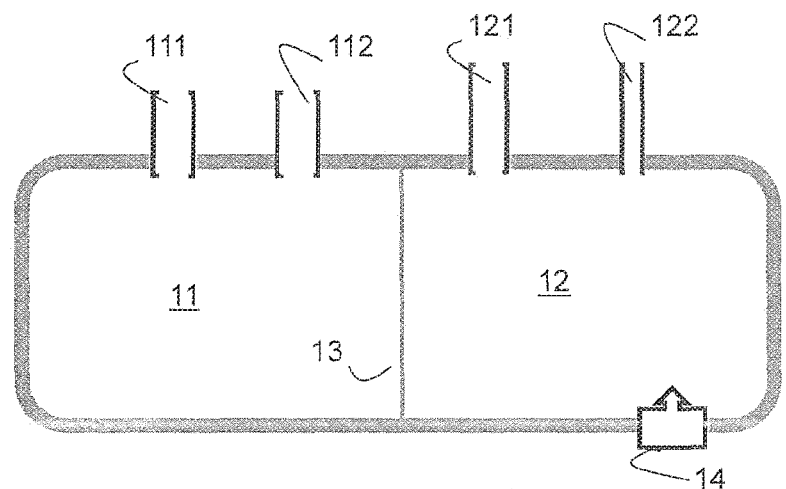
FIG. 1 is a schematic cross-section of a two chamber pump in accordance with an example of the invention.

A first schematic representation of a basic device in accordance with an example of the invention is shown in FIG. 1.

The device of FIG. 1 is a two chamber pump 10 having a fluid pump chamber 11 and a driver chamber 12. The walls of the chambers are made of a silicone based material. The inter-chamber wall 13 is made of a reduced thickness compared to the exterior walls. Ports 121, 122 in the exterior walls of the driver chamber provide a supply path to a fuel and oxidant reservoir (not shown) and an exhaust path for reaction products. Ports 111, 112 in the exterior wall of the fluid pump chamber provide inlet and outlet, respectively, for fluid to be pumped.

An ignition device 14 is integrated into one exterior wall and at least partly exposed to the interior of the driver chamber 12. The device can include for example two electrodes connected to two poles of a voltage source in a manner similar to a spark plug.

Figure 2A:
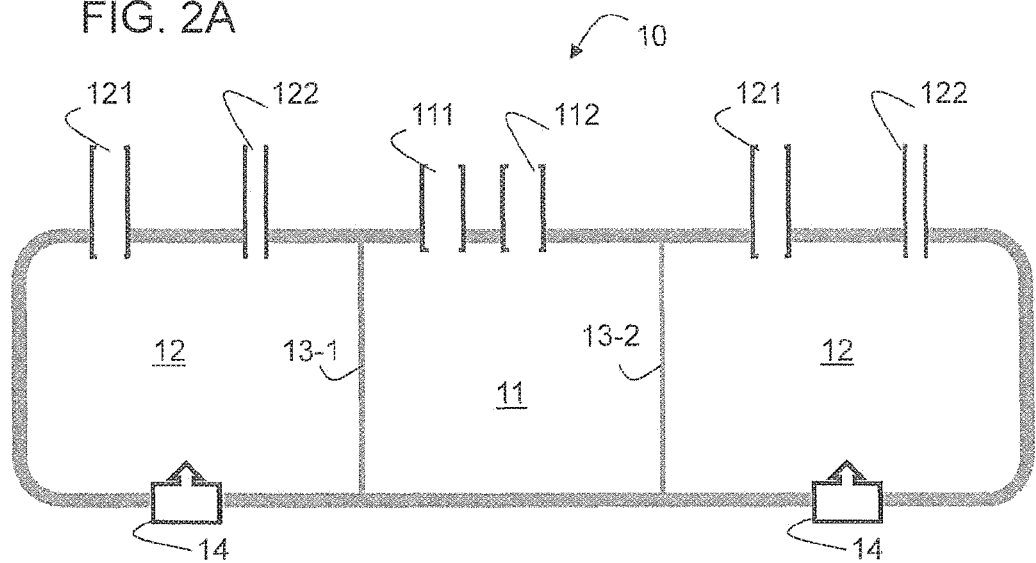
FIGS. 2A-2C are schematic cross-sections of a three chamber pump in accordance with an example of the invention during three different stages of a pump cycle.
Figure 2B:
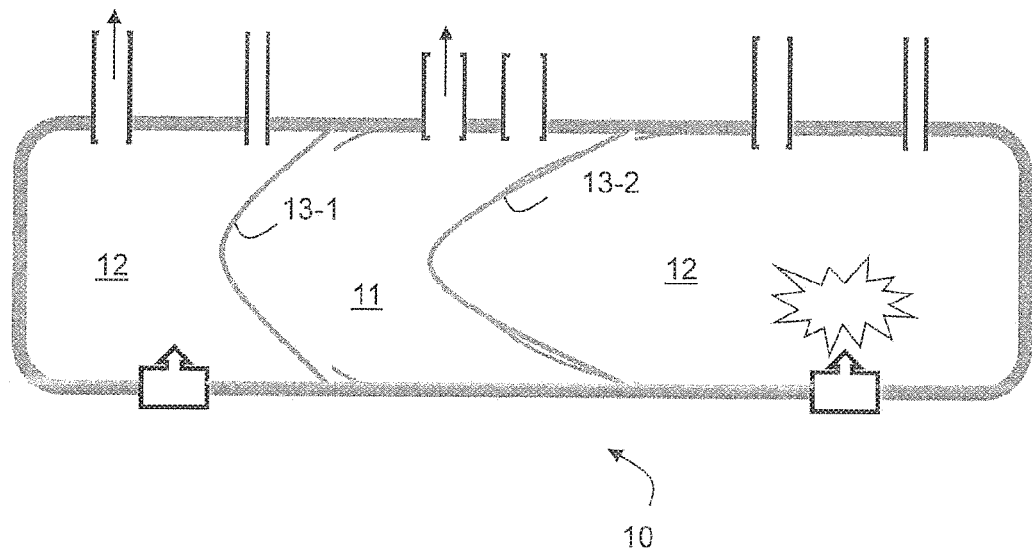
Figure 2C:
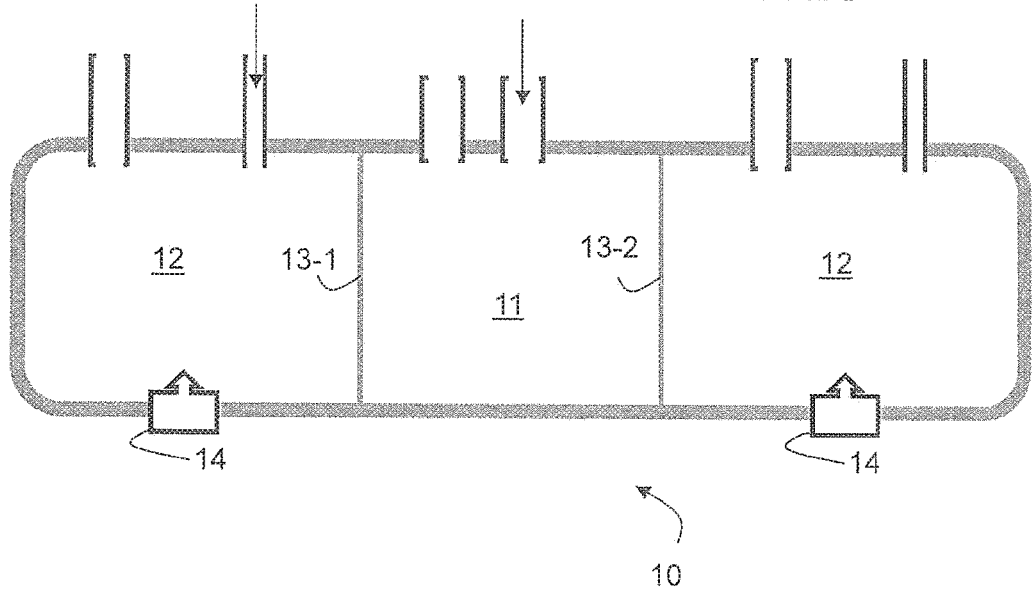
Figure 3:
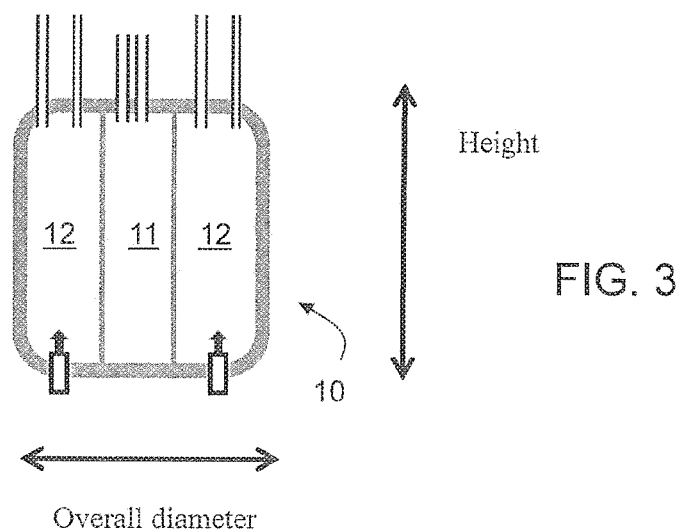
FIG. 3 is a schematic cross-section of another three chamber pump in accordance with an example of the invention.

Elements of a three chamber pump in accordance with an example of the invention are shown in FIGS. 2A to 2C. The pump differs from the pump of FIG. 1 by addition of a second drive chamber 12. Hence the pump has two inter-chamber walls 13-1 13-2. As the elements of the second driver chamber 12 are identical to those of the first driver chamber already described above, the same numerals have been used to denote the same elements.

In a preferred geometry of a three chamber pump, one chamber serves as a driver chamber, one as a liquid pumping chamber and one chamber assists the aspiration of air as oxidant, for example for use in a later stage of a pump operation cycle.

This intake of air can be used advantageously in an embodiment where the two driver chambers 12 that are each used in a pump cycle as described in further detail below alternating as exhaust/intake chamber, i.e., first as expansion chamber and in the following pump cycle as exhaust/intake chamber, and so forth. The chambers 12 may either be arranged in a linear way, with the fluid pumping chamber 11 in the middle, or, the two driver chambers may be next to one another, sharing a common wall (driver 1/driver 2) and both a common wall with the pumping chamber. The wall thickness of (driver 1/driver 2) will be different from the wall (driver 1 or 2/pumping). Chambers may include sensors to measure fluid concentration levels etc.

A pump as shown in FIG. 2 can be operated according to the following cyclic steps:

Step 1: The first driver chamber 12 is filled with a ready-to-react fuel mixture whilst the pump chamber 11 and second driver chamber 12 are in a relaxed state. This state is illustrated in FIG. 2A.

Step 2: The fuel mixture in the first driver chamber 12 is ignited and its volume is growing. At its maximum expansion, the volume of the gas contained in this first driver chamber is between 1.3 to 3 times the volume before ignition. In this expansion step both the pumping chamber is pumping fluid and the second driver chamber 12 exhausts reaction products of a previous cycle. This is a result of a deformable, soft design, where the pumping chamber can be significantly deformed, hence also changing the volume of its adjacent second driver chamber. This state is illustrated in FIG. 2B showing the deformation of the inter-chamber walls 13-1 and 13-2. The liquid displacement (pump volume) is (the pump chamber volume displacement due to deformation of the wall between first driver chamber 12 and the fluid pump chamber 13) minus (the volume displacement due to expansion of the pumping chambers wall to the second driver chamber) minus (the volume displaced at walls facing the outside of the pump). Typical liquid displacements as a result of a single pumping event (i.e. one ignition in a driver chamber) are between 0.2 to 0.8 times the volume of the liquid pumping chamber when relaxed.

Valves at the entry and exit points of the individual chambers direct the flow of gas or liquids typically in a unidirectional way and avoid backflow of liquids or gases. Suitable valves are known in this field and can consist of ball valves or flap-based valves, amongst others.

Step 3: System relaxes to its initial state as the elastic material restores all chambers of the pump back to their most relaxed form. The first driver chamber 12 cools down whilst the fluid pumping chamber 11 sucks in fluid up to its relaxed position (usually straight walls) and the second driver chamber 12 refills by taking in the fuel mixture. The fuel mixture can be injected or sucked in into second driver chamber 12. This state is illustrated in FIG. 2C which is identical to FIG. 2A with the role of fuel-filled and exhaust filled driver chamber 12 reversed.

In the following steps the function of the first and second driver chamber 12 is reversed and hence:

Step 4: The first driver chamber 12 is compacted and exhausts the burned fuel mixture whilst the pumping chamber 11 is pumping out the fluid and the second driver chamber 12 is expanding after an ignition and reaction of the fuel mixture Step 5: The first driver chamber 12 relaxes again and takes in the fuel mixture and the pumping chamber refills and the second driver chamber 12 cools down and exhausts the reaction products.

Step 6: The system at this step is now equal to the system at the start of Step 1 thus terminating one pumping cycle.

In the cycle fuel and oxidants are provided and exhaust exits the driver chamber through the ports 121, 122. It is preferred to use at least one first port 121 solely for fuel supply and at least one second port 122 solely as exit for the exhaust of the reaction products. The flow through the port can be controlled by valves, particularly one-way valves (not shown) as mentioned above.

In addition to such valves or alternatively, the deformation used for the pumping can also be used to provide a valve-like action on supply and/or exhaust tubes. For example deformable sections of tubular connectors to the ports can be used, which are closed and opened through the expansion or compression of driver chambers. The soft design of the pump hence permits to have deformable sections of tubing at inlet or exit of gas/liquid ports. Deformation due to use of a driver chamber then alters the opening in such deformable sections, hence permitting some control on the flow through that section.

The ports can optionally be open or covered by a permeable membrane, for example a hydrophilic, semipermeable membrane. Due to its hydrophilicity, the membrane can permit slow transfer of water out of the liquid pump. In such a design, water as a waste product is slowly released out of the driver chamber similar to a drain. This exploits an effect similar to wetted fabric (e.g. woven cotton), which is known to be nearly impermeable for air, while water can flow almost freely through it. This effect is best known when cotton cloth get soaked with water and held under water with air trapped inside. Driving air through wetted cotton requires significant pressure. Since the pressure depends on the mesh width of the cloth, finer fabrics withstand higher pressure. This allows the adaptation of the membrane to a given design or purpose.

The fuel can include for example a volatile organic, combustible liquid and hydrogen peroxide or of a gas mixture such as hydrogen gas and air.

The fuel can be ignited electrically using sparks as generated by the ignition controller 14. Alternatively or in addition, the ignition controller can include a catalyst, such as a noble metal or metal composition including a noble metal, igniting the fuel mixture at defined concentration levels of fuel and oxidant.

In a specific form of the invention, a self-igniting effect is used, well known from the ignition of hydrogen containing gas mixtures on fine powdered noble metals, particularly platinum, as platinum sponge. This effect is known from the so called Döbereiner' Fire lighter. The control on the pumping cycle is then possible through timing the inflow of reactants (e.g. hydrogen and air): If fuel (e.g. hydrogen) is being fed very slowly into the driver chamber, it takes more time to reach critical hydrogen concentration for ignition then when the hydrogen flow is higher. Hence, the frequency of the ignition and hence pumping can be controlled to a certain extent by the hydrogen feed rate.

For certain applications, particularly in artificial hearts, a four chamber design can be advantageous, as it resembles the biological design of the human heart. However, an even higher number of chambers may be used.

In FIG. 4 there is shown an example of a pump with an aspect ratio of 1:1 between height and diameter. Such an aspect ratio leading to a relatively shallow volume of the chamber and long inter-chamber walls is preferred to increase the efficiency of the pump.

Depending on the pressure and volume of the liquid to be conveyed, other designs are preferred, e.g. concentric arrangement of the chambers. Here, the geometry of the natural, human heart chamber can be better matched. The pumping chamber is then an asymmetric chamber as in a biological heart chamber, and at least partly surrounded by a driver chamber in a geometry similar to the natural heart muscle. This arrangement is very efficient to transform the expansion of the driver chamber into pushing/compaction of the liquid chamber. Ignition and feed ports are then preferably located at the outside of this concentric arrangement.

For a complete heart replacement, two pumping chambers similar to the natural human heart are needed. There, the arrangement of the natural human heart can be used as a guiding principle. The two pumping chambers are dissimilar in size (the left and right heart chambers are of different strength as the lung branch of the blood circulation has less flow resistance and hence a lower pressure than the larger main branch of the heart, with higher liquid pressure). Both chambers are each surrounded at least to a large extent by a driver chamber. As a result of these constraints, the driver chamber takes the volume between an approximately cylindrical pump chamber in the center, and the outer envelope or wall of the pump itself. Typical chambers will be 2-5 times longer (if the pump is located in a similar fashion as a human heart in a standing human being) then wide. The aspect ratio of 2:1-5:1 and design is similar to the human heart muscle. As stated above, the outside wall of the pump are more resistant to expansion than the wall separating a driver chamber from a pumping chamber.

Figure 4A:
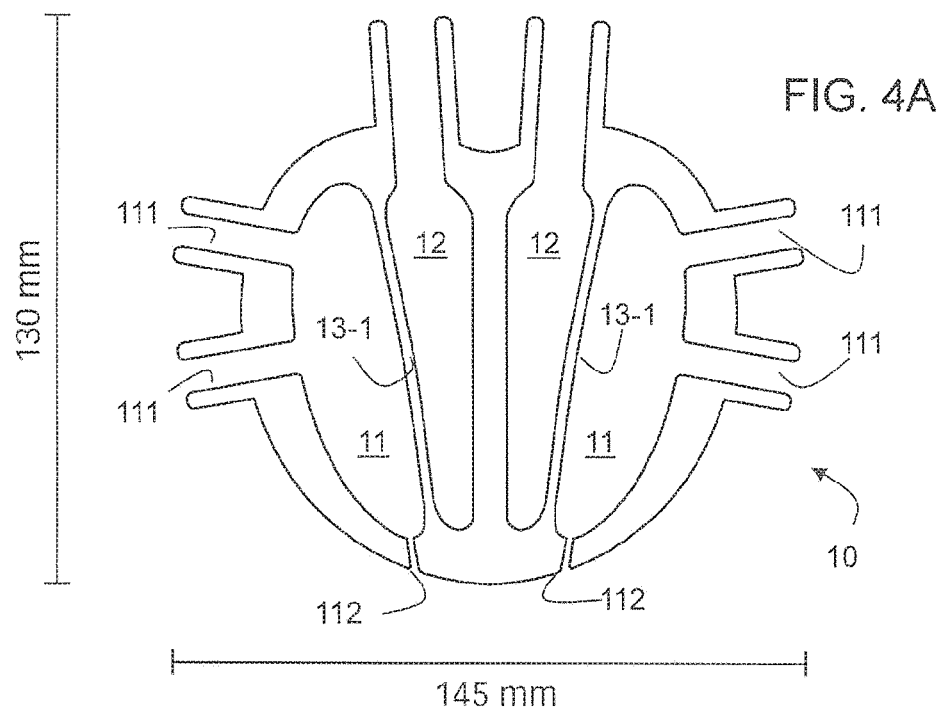
FIGS. 4A-4C are schematic cross-sections of pump designs shaped as heart replacement in accordance with further examples of the invention.
Figure 4B:
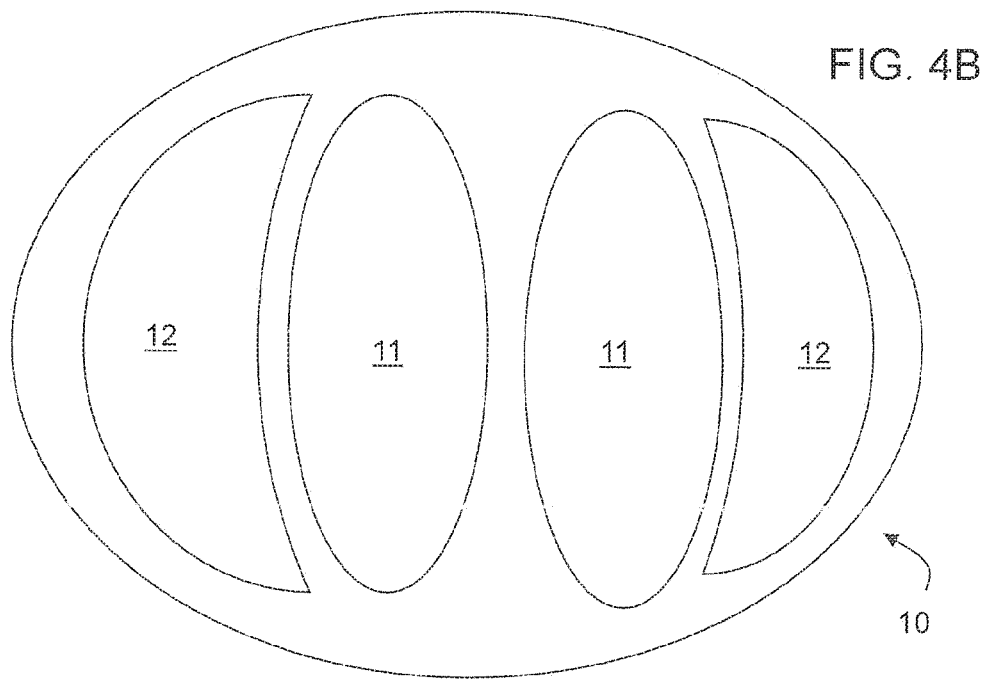
Figure 4C:
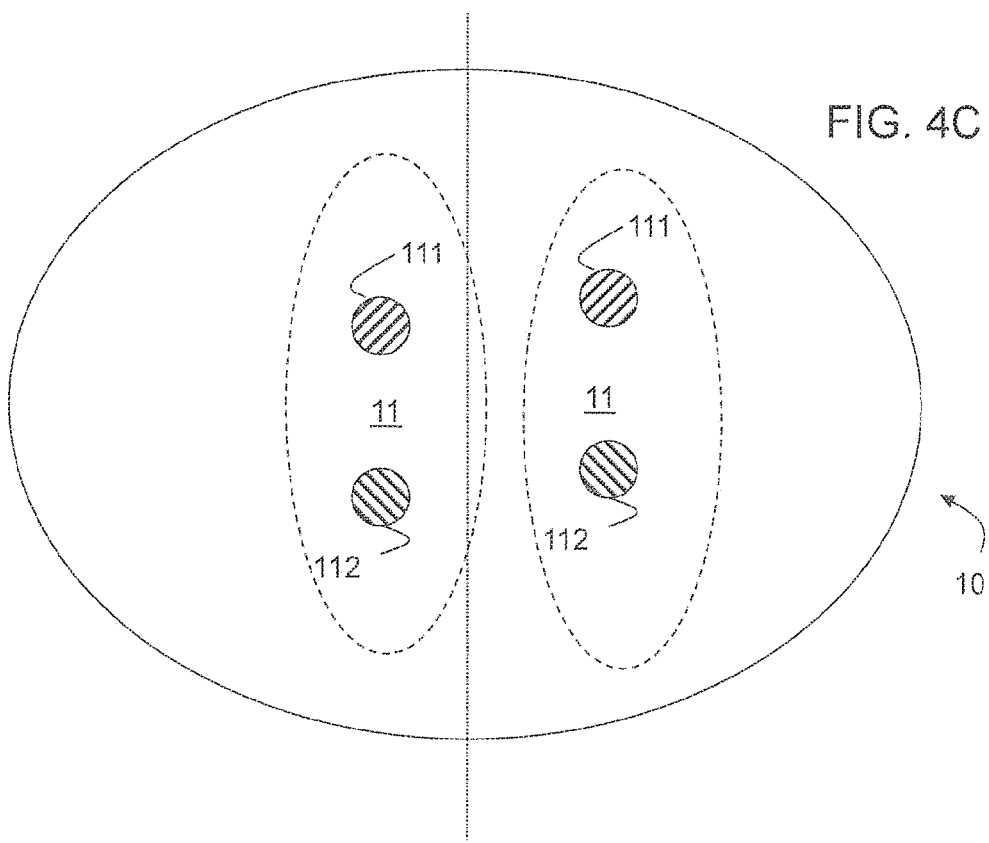

Examples of four chamber pumps with these aspect ratios are shown in FIG. 4A-4C. In the example of FIG. 4A, the pump 10 has two inner driver chambers 12 and two outer fluid pump chambers 11. Each of the fluid pump chambers 11 have two fluid intake ports 111 and one exit port 112. The material is a room temperature vulcanizing silicone Neukasil™ RTV23 (Vulcanizer VN A 7, vulcanized at 50° C.) as provided by Altropol Kunststoffe GmbH, Stockelsdorf, Germany. The material is extremely flexible having breaking elongation of about 1000%.

The shape as shown can be manufactured using for example investment casting with the cast from ABS generated through a 3D printing process and later dissolved in an acetone solution.

The pump has a material volume of 485 cm^3 of silicone (weight: 530 g) with the volume of a driver chamber 11 95 cm^3 and the volume of a pumping chamber 12 60 cm^3. The inter-chamber walls 13-1, 13-2 have a thickness of 3 mm while the exterior walls have a thickness of 8 mm.

For pumping, the inner driver chambers 12 are alternatingly filled with a methane/air mixture and ignited at (4.8 Volt, 3 A) using a commercially available electronic igniter. The driver chambers are filled with a gas flow 0.22 L/min of CH4 (at 0.25 Hz pumping frequency) and 2.2 L/min Air (at 0.25 Hz pumping frequency). The replacement of burned gas volume in a driver chamber is approximately 85% at the flow rate as stated. If the pump is operated at higher frequency (e.g. 1 Hz), the gas flow rates and ignition are increased to 0.9 L/min of CH4 (at 1.0 Hz pumping frequency) and 9 L/min Air.

In the example of FIGS. 4B and 4C the relative arrangement of pumping chambers and driver chambers is reversed compared to the 4 chamber pump of FIG. 4A. Hence, the pumping chambers 11 occupy an essentially cylindrical core volume in the center of the pump 10, whilst the driver chambers 12 are located between the core volume and the outer walls of the pump.

The cross-section of FIG. 4B shows a layer of the pump 10 at about mid-height. One of the driver chambers 12 is larger than the other, thus rendering the design asymmetric. The second cross-sectional view (FIG. 4C) is taken from above the pump. Here the locations of the interior pump chambers 11 are indicated as dashed line. A dotted line shows the location of the vertical central plane of the pump thus emphasizing the asymmetric design of the pump. Each pump chamber 11 has an inlet port 111 and an outlet port 112 to provide pumping fluid transport into and out of the pump.

While there are shown and described presently preferred embodiments of the invention, it is to be understood that the invention is not limited thereto but may be otherwise variously embodied and practised within the scope of the following claims.

The invention claimed is:

1. Peristaltic pump driven by a chemical reaction between a fuel and an oxidant comprising
    at least one fluid pump chamber and
    a first driver chamber separated from the fluid pump chamber by a first elastic wall,
    wherein the first driver chamber comprises one or more ports for fuel or oxidant containing fluids to enter and for exhaust fluids to leave the first driver chamber, and
    wherein the first driver chamber expands after a first chemical reaction between fuel and oxidant in said first driver chamber.

2. The pump of claim 1 comprising at least two pairs of chambers each comprising a fluid pump chamber and a first driver chamber separated from the fluid pump chamber by a first at least partly elastic wall.

3. The pump of claim 2 wherein the fluid pump chamber of each pair is located closer to the geometrical center of the pump than its associated first driver chamber.

4. The pump of claim 1 comprising a second driver chamber separated from the fluid pump chamber or the first driver chamber by a second at least partly elastic wall wherein the second driver chamber expands after a chemical reaction between fuel and oxidant different from the first chemical reaction expanding the first driver chamber.

5. The pump of claim 1, further comprising several driver chambers and an ignition controller adapted and structured to initiate the chemical reactions expanding said driver chambers at different times within the duration of one period of a cyclic process.

6. The pump of claim 1, wherein said first driver chamber comprises catalytic material to promote the reaction.

7. The pump of claim 1, wherein one or more interior walls comprise an elastomeric material.

8. The pump of claim 1, comprising of at least 80% of an elastomeric material.

9. The pump of claim 1 made essentially of a homogeneous elastomeric material.

10. The pump of claim 7, wherein the elastomeric material is selected from a group of nitrile (NBR), Hypalon, Viton, silicone, PVC, EPDM, EPDM with polypropylene, polyurethane and natural rubber and mixtures and blends thereof.

11. The pump of claim 1, comprising at least one wall section having a base material and fibrous material embedded in the base material.

12. The pump of claim 1 wherein at least said fluid pump chamber, said driver chamber(s) and said ports are of a single material.

13. Use of the pump in accordance with claim 1, in farming, hazardous fluids or fluids loaded with solid particles.

14. Body implant, particularly artificial heart, comprising a pump in accordance with claim 1.

15. The pump of claim 1 wherein the first driver chamber comprises an ignition device integrated into an exterior wall and at least partly exposed to the interior of the first driver chamber.

16. The pump of claim 1 wherein said one or more ports are in an exterior wall of the first driver chamber for fuel or oxidant containing fluids to enter and for exhaust fluids to leave the chamber.

* * * * *